United States Patent
Chen et al.

(10) Patent No.: US 10,555,691 B2
(45) Date of Patent: Feb. 11, 2020

(54) VITAL SIGNS DETECTING DEVICE AND A METHOD FOR DETECTING VITAL SIGNS

(75) Inventors: Zhi Hao Chen, Singapore (SG); Ju Teng Teo, Singapore (SG); Xiufeng Yang, Signapore (SG)

(73) Assignee: Agency for Science Technology and Research, Singapore (SG)

( * ) Notice: Subject to any disclaimer, the term of this patent is extended or adjusted under 35 U.S.C. 154(b) by 1016 days.

(21) Appl. No.: 13/389,226

(22) PCT Filed: Apr. 21, 2010

(86) PCT No.: PCT/SG2010/000162
§ 371 (c)(1),
(2), (4) Date: Apr. 20, 2012

(87) PCT Pub. No.: WO2011/016778
PCT Pub. Date: Feb. 10, 2011

(65) Prior Publication Data
US 2012/0203117 A1    Aug. 9, 2012

Related U.S. Application Data

(60) Provisional application No. 61/231,771, filed on Aug. 6, 2009.

(51) Int. Cl.
*A61B 5/08*    (2006.01)
*A61B 5/0205*    (2006.01)
(Continued)

(52) U.S. Cl.
CPC ................... *A61B 5/1127* (2013.01)

(58) Field of Classification Search
CPC ..... A61B 5/0205; A61B 5/024; A61B 5/0816; A61B 5/113; A61B 5/11
(Continued)

(56) References Cited

U.S. PATENT DOCUMENTS 4,822,135 A    4/1989  Seaver
5,134,281 A *  7/1992  Bryenton ............. A61B 5/1073
                                                        250/227.14
(Continued)

FOREIGN PATENT DOCUMENTS

WO          0153787 A1    7/2001

OTHER PUBLICATIONS

International Preliminary Report of Patentability of PCT Application No. PCT/SG2010/000162 dated Nov. 29, 2011 (13 pgs.).
(Continued)

*Primary Examiner* — Etsub D Berhanu
(74) *Attorney, Agent, or Firm* — Conley Rose, P.C.

(57) ABSTRACT

A vital signs detecting device and a method for detecting vital signs are provided. The vital signs detecting device comprises a detection unit; a multimode optical fiber configured to be connected to a light source and to the detection unit; a mechanical structure configured for receiving a pressure exerted by a person's body as a result of one or more of a group consisting of a movement of the person's body, a respiratory action of the person's body and a heart beat action of the person's body and to cause microbending of the multimode optical fiber under the exerted pressure and; wherein the multimode optical fiber is disposed between first and second sets of microbending elements of the mechanical structure substantially in a direction of the exerted pressure.

8 Claims, 17 Drawing Sheets

(51) Int. Cl.
*A61B 5/113* (2006.01)
*A61B 5/11* (2006.01)

(58) Field of Classification Search
USPC ........................................ 600/484, 534, 595
See application file for complete search history.

(56) References Cited

U.S. PATENT DOCUMENTS

| | | | |
|---|---|---|---|
| 5,212,379 | A | 5/1993 | Nafarrate et al. |
| 5,241,300 | A * | 8/1993 | Buschmann ......... A61B 5/1135 340/531 |
| 5,291,013 | A | 3/1994 | Nafarrate et al. |
| 5,818,982 | A | 10/1998 | Voss et al. |
| 6,498,652 | B1 | 12/2002 | Varshneya et al. |
| 6,711,330 | B1 | 3/2004 | Donlagic et al. |
| 7,196,317 | B1 * | 3/2007 | Meissner, II .......... A61B 5/1115 250/227.14 |
| 2005/0059868 | A1 * | 3/2005 | Schurman .......... A61B 5/14551 600/323 |
| 2009/0306520 | A1 * | 12/2009 | Schmitt ................ A61B 5/0066 600/476 |

OTHER PUBLICATIONS

International Search Report for Application No. PCT/SG2010/000162 dated Jul. 20, 2010 (4 pgs.).
Rothmaier Markus et al. "Photonic texiles for pulse oximetry" Optics Express 12973, vol. 16, No. 17, pp. 12973-12986, Aug. 18, 2008 (14 pgs.).
Rothmaier Markus et at "Textile Pressure Sensor made of flexible Plastic Optical Fibers" Sensors ISSN 1424-8220, vol. 8, pp. 4318-4329, Jul. 25, 2008 (12 pgs.).
Wang et al "A shear and plantar pressure sensor based on fiber-optic bend loss" Journal of Rehabilitation Research & Development, vol. 42, No. 3, pp. 315-326, May/Jun. 2005 (11 pgs.).

* cited by examiner

VITAL SIGNS DETECTING DEVICE AND A METHOD FOR DETECTING VITAL SIGNS

FIELD OF INVENTION

The present invention relates broadly to a vital signs detecting device and a method for detecting vital signs.

BACKGROUND

Breathing rate/heart beat rate/body movement are typical vital signs parameters used in clinical monitoring of patients. Heart and lung diseases typically affect breathing rate/heart beat rate. It may also be desired to know the body movement of bed ridden patients within a specific period of time. Therefore, monitoring of these vital signs parameters can be a significant diagnostic method in planning of medical care.

Electrical sensors have typically been used for monitoring of the parameters. For example, US 2007/0008156 describes using piezoelectric sensors. However, it has been recognized that electrical sensors are not sensitive enough to distinguish between, for example, shallow breathing and no breathing. In addition, electrical sensors are typically prone to electromagnetic interference (EMI), which can be a significant problem in certain clinical examinations, e.g., during magnetic resonance imaging (MRI) examinations.

As an alternative, use of optical fiber sensors has been explored. Optical fiber sensors are inherently immune from electromagnetic interference and are chemically inert. In "Optical fibre sensors embedded into medical textiles for heathcare monitoring", *IEEE Sensor J.* 8 (7), 1215-1222, 2008, Grillet et al used a macrobending sensor. The sensor is a single mode fiber in a belt form for measuring respiratory rate. Although the interrogation is relatively simple and requires only low cost and compact components, a macrobending sensor typically has low sensitivity such that even if such a sensor is embedded within a bed, it is typically difficult to detect chest wall movement during breathing. The differences between macrobending and microbending in optical fibers is established. Macrobending typically causes light to leak out of a fiber due to macroscopic deviations of the fiber's axis from a straight fine. On the other hand, microbending is typically due to mechanical stress on a fiber that introduces local discontinuities which can result in light leaking from the core of the fiber to a cladding via mode coupling. In U.S. Pat. No. 6,498,652, although an optical phase interferometry-based fibre optic sensor was found to have higher sensitivity, the sensor system used is complex, leading to cost increases that may inhibit practical implementation. Grillet et al also tested fibre Bragg grating (FBG)-based sensors and optical time-domain reflectometer (OTDR)-based sensors for breathing rate measurement. However, it has been found that both such sensing systems are too complex and expensive.

In "A smart bed for non-intrusive monitoring of patient physiological factors", *Meas. Sci. Technol.* 15, 1614-1620, 2004, Spillman et al proposed using a fibre optic statistical mode (STM) sensor and a high order mode excitation (HOME) sensor for breathing rate/heart beat measurements. However, it has been found that these sensors require highly coherent light sources and a bulky high order mode generator. In "Application of long period grating sensors to respiratory function monitoring", *Proc. SPIE,* 5588, 148-156, 2004, Allsop et al used a long period grating-based sensor to monitor breathing rate. However, it has been found that the system is too complex and expensive. In "Monitoring of the Heartbeat Sounds using an Optical Fiber Bragg Grating Sensor", IEEE Sensor conference, pp 306-309, 2005, Gurkan et al proposed using a FBG sensor for heart beat measurement. It has been found that although a FBG sensor-based system has relatively good sensitivity, the system cost is significantly high.

Therefore, there exists a need for a vital signs detecting device and a method for detecting vital signs that seek to address at least one of the problems.

SUMMARY

In accordance with an aspect of the present invention, there is provided a vital signs detecting device, the device comprising a detection unit; a multimode optical fiber configured to be connected to a light source and to the detection unit; a mechanical structure configured for receiving a pressure exerted by a person's body as a result of one or more of a group consisting of a movement of the person's body, a respiratory action of the person's body and a heart beat action of the person's body and to cause microbending of the multimode optical fiber under the exerted pressure and; wherein the multimode optical fiber is disposed between first and second sets of microbending elements of the mechanical structure substantially in a direction of the exerted pressure.

The first set of microbending elements may be comprised in a first layer of the mechanical structure and the second set of microbending elements may be comprised in a second layer and further wherein the multimode optical fiber may be disposed between the first and second layers.

The first and second layers may each comprise a mesh-like structure.

The mechanical structure may be interwoven with the multimode optical fiber such that the first set of microbending elements may be disposed on a top surface of the multimode optical fiber and the second set of microbending elements may be disposed on a bottom surface of the multimode optical fiber.

The mechanical structure may comprise a mesh-like structure.

The device may further comprise the light source for inputting light into the multimode optical fiber and the detection unit may comprise a light detection unit for detecting light modulation in the multimode optical fiber.

The device may further comprise a mirror attached to the multimode optical fiber at one end thereof for reflecting light to the other end of the optical fiber.

The device may further comprise a 1×2 fiber coupler for connecting the light source and the light detection unit to the multimode optical fiber at said other end of the optical fiber.

The device may further comprise a 1×2 fiber coupler connected to the multimode optical fiber at one end thereof, the 1×2 fiber coupler configured for redirecting light to the other end of the optical fiber.

The device may further comprise a second 1×2 fiber coupler for connecting the light source and the light detection unit to the multimode optical fiber at said other end of the optical fiber.

In accordance with another aspect of the present invention, there is provided a vital signs detecting device, the device comprising a detection unit; a multimode optical fiber configured to be connected to a light source and to the detection unit; a mechanical structure configured for receiving a pressure exerted by a person's body and to cause microbending of the multimode optical fiber under the exerted pressure and; wherein the detection unit is adapted for determining at least a heart rate of the person based on light intensity variations caused by bending losses induced by the microbending.

The detection unit may comprise a signal processing unit.

The signal processing unit may be configured to extract information of at least one of a group consisting of heart beat rate, breathing rate and body movement.

The body movement information may be extracted based on a signal deviation tracking process implemented in the signal processing unit.

For an application associated with breathing, the breathing rate information may be extracted based on a signal filtering process and at least one process selected from a group consisting of peak detection, valley detection, amplitude detection, Fast Fourier Transform and Wavelet analysis, the processes being implemented in the signal processing unit.

For an application associated with heart beat, the heart beat rate information may be extracted based on a signal filtering process and at least one process selected from a group consisting of peak detection, valley detection, amplitude detection, Fast Fourier Transform and Wavelet analysis, the processes being implemented in the signal processing unit.

The signal processing unit may comprise a display function for displaying the extracted information.

The signal processing unit may have an alarm function implemented thereon for activating an alarm based on the extracted information.

In use, the multimode optical fiber and the mechanical structure may function as a fiber mode converter.

In accordance with another aspect of the present invention, there is provided a method for detecting vital signs, the method comprising providing a detection unit; connecting a multimode optical fiber to a light source and to the detection unit; providing a mechanical structure for receiving a pressure exerted by a person's body as a result of one or more of a group consisting of a movement of the person's body, a respiratory action of the person's body and a heart beat action of the person's body and to cause microbending of the multimode optical fiber under the exerted pressure; and wherein the multimode optical fiber is disposed between first and second sets of microbending elements of the mechanical structure substantially in a direction of the exerted pressure.

The first set of microbending elements may be comprised in a first layer of the mechanical structure and the second set of microbending elements may be comprised in a second layer and further wherein the multimode optical fiber may be disposed between the first and second layers.

The first and second layers may each comprise a mesh-like structure.

The mechanical structure may be interwoven with the multimode optical fiber such that the first set of microbending elements may be disposed on a top surface of the multimode optical fiber and the second set of microbending elements may be disposed on a bottom surface of the multimode optical fiber.

The mechanical structure may comprise a mesh-like structure.

The method may further comprise inputting light into the multimode optical fiber and detecting light modulation in the multimode optical fiber.

The method may further comprise attaching a mirror to the multimode optical fiber at one end thereof for reflecting light to the other end of the optical fiber.

The method may further comprise using a 1×2 fiber coupler for connecting the light source and a light detection unit to the multimode optical fiber at said other end of the optical fiber.

The method may further comprise connecting a 1×2 fiber coupler to the multimode optical fiber at one end thereof, the 1×2 fiber coupler configured for redirecting light to the other end of the optical fiber.

The method may further comprise using a second 1×2 fiber coupler for connecting the light source and a light detection unit to the multimode optical fiber at said other end of the optical fiber.

In accordance with another aspect of the present invention, there is provided a method for detecting vital signs, the method comprising providing a detection unit; connecting a multimode optical fiber to a light source and to the detection unit; providing a mechanical structure for receiving a pressure exerted by a person's body and to cause microbending of the multimode optical fiber under the exerted pressure; and determining at least a heart rate of the person based on light intensity variations caused by bending losses induced by the microbending.

The method may further comprise extracting information of at least one of a group consisting of heart beat rate, breathing rate and body movement from the light intensity variations.

The body movement information may be extracted based on a signal deviation tracking process.

For an application associated with breathing, the breathing rate information may be extracted based on a signal filtering process and at least one process selected from a group consisting of peak detection, valley detection, amplitude detection, Fast Fourier Transform and Wavelet analysis.

For an application associated with heart beat, the heart beat rate information may be extracted based a signal filtering process and at least one process selected from a group consisting of peak detection, valley detection, amplitude detection, Fast Fourier Transform and Wavelet analysis.

The method may further comprise displaying the extracted information.

The method may further comprise activating an alarm based on the extracted information.

The multimode optical fiber under the exerted pressure may function as a fiber mode converter.

In accordance with another aspect of the present invention, there is provided a data storage medium having computer code means stored thereon for instructing a computing device to execute a method for vital signs detection, the method comprising the steps of receiving an optical signal from a multimode optical fiber; and determining at least a heart rate of a person based on light intensity variations caused by bending losses induced by a mechanical structure configured for receiving a pressure exerted by the person's body and to cause microbending of the multimode optical fiber under the exerted pressure.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

In an example embodiment, a vital signs detecting/sensing device is provided. The device comprises a fiber optic sensor mat and an interrogator for vital signs measurement. The sensor mat is configured such that a top and a bottom layer each comprises large area mesh-like structures which are made of polyester fiber. The sensor mat further comprises a section of a multimode optical fiber disposed in between the top and bottom layers. The interrogator comprises a light source, a detector, and a signal processing unit. The interrogator further comprises a display and an alarm function for reporting and/or alerting users to the measurement.

In the example embodiment, the section of multimode optical fiber is embedded in between two polyester fiber sheets with large area mesh-like structures. The polyester mesh-like structures provide protection to the multimode optical fiber. In addition, the mesh-like structures form a mechanical structure for creating a microbending effect on the multimode optical fiber. The mechanical structure can receive a pressure exerted by a person's body as a result of one or more of a group consisting of a movement of the person's body, a respiratory action of the person's body and a heart beat action of the person's body and can cause microbending of the multimode optical fiber under the exerted pressure. Thus, in the example embodiment, the multimode optical fiber is disposed between first and second sets of microbending elements of the mechanical structure substantially in a direction of the exerted pressure. In this example embodiment, the first set of microbending elements are comprised in the top layer of the sensor mat and the second set of microbending elements are comprised in the bottom layer of the sensor mat. In the example embodiment, using the described sensor mat, measurement of breathing rate is not sensitive to body movement, or car movement if the sensor mat is installed in a moving car.

In the example embodiment, bending losses due to the microbending effect can be monitored for extracting information. Further, the device can advantageously be adapted to determine heart beat rate.

Furthermore, by disposing the multimode optical fiber between first and second sets of microbending elements of the mechanical structure, the microbending effect achievable can be increased. This can provide advantages over a configuration providing bending elements acting on only one side of a fiber such as a configuration with an optical fiber disposed on a layer of microbending elements.

In a microbend fiber optic sensor, mechanical perturbation of a multimode fiber waveguide causes a redistribution of light power among the modes in the fiber. The more severe the mechanical perturbation or bending, the more light is coupled to higher order modes or even radiation modes and is lost. A microbend fiber optic sensor is a light intensity sensor and light intensity decreases with mechanical bending.

Figure 1:
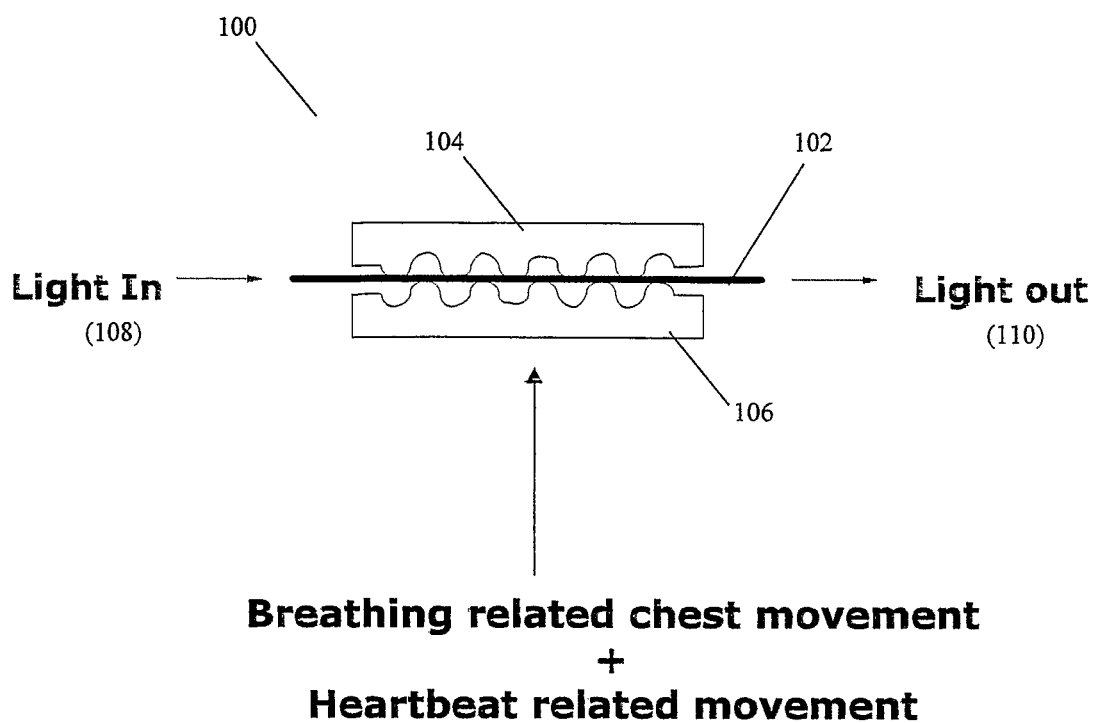
FIG. 1 is a schematic diagram illustrating a sensor mat in an example embodiment.

FIG. 1 is a schematic diagram illustrating a sensor mat 100 in an example embodiment. A section of multimode optical fiber 102 is embedded between mesh-like structures 104, 106. Light is input (at numeral 108) into one end of the multimode optical fiber 102 and extracted (at numeral 110) from another end of the multimode optical fiber 102. The mesh-like structures 104, 106 can create a microbending effect on the section of multimode optical fiber 102. When the sensor mat 100 is used, movement such as breathing related chest movement or heartbeat related movement can be detected via the created microbending effect and the resultant light extracted (at numeral 110). Thus, in the example embodiment, light is modulated via the microbending effect when there is e.g. breathing/heart beating imparted to the sensor mat 100.

It will be appreciated that FIG. 1 shows an embodiment without a user lying on the sensor mat. In use, for example when a user is lying on the sensor mat 100, the mesh-like structures 104, 106 interlink due to the user lying on the sensor mat 100 and the section of multimode optical fiber 102 is bent. Thus, the configuration of the structures 104, 106 and the section of multimode optical fiber 102 functions as a fiber mode converter. A fiber mode converter can stabilize modes propagating in the multimode optical fiber 102 by bending the optical fiber 102 that causes efficient mode coupling. There are a plurality of modes propagated in the multimode optical fiber 102 and any external perturbations on the optical fiber 102 can cause a redistribution of modal power. When the multimode optical fiber 102 is bent, light transmitted along the optical fiber 102 may attenuate. The bending losses in the multimode fiber 102 can be used to obtain desired information. For example, when the multimode optical fiber 102 is imposed with curvature bends, the light loss increases with the number of bending lengths and as the bending radius decreases.

Figure 2:
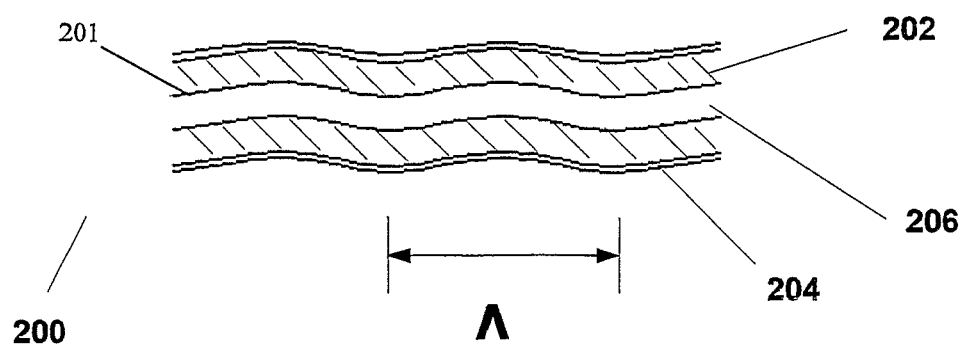
FIG. 2 is a schematic diagram showing a microbending multimode fiber under deformation in an example embodiment.

FIG. 2 is a schematic diagram 200 showing a microbending multimode fiber 201 under deformation in an example embodiment. The microbending multimode fiber 201 comprises a cladding 202 and a buffer layer 204 that surrounds the cladding 202. The cladding 202 surrounds the fiber core

206. In the example embodiment, the optimized sensor sensitivity can be obtained based on the equation $$\Lambda = \frac{\sqrt{2}\,\pi a n_0}{NA}$$

for step-index fibers, or $$\Lambda = \frac{2\pi a n_0}{NA}$$

for graded-index fibers, where $\Lambda$ is critical periodicity of fiber deformation, $n_0$ is the refractive index of the core, a is the core radius, and NA is the numerical aperture.

Figure 3:
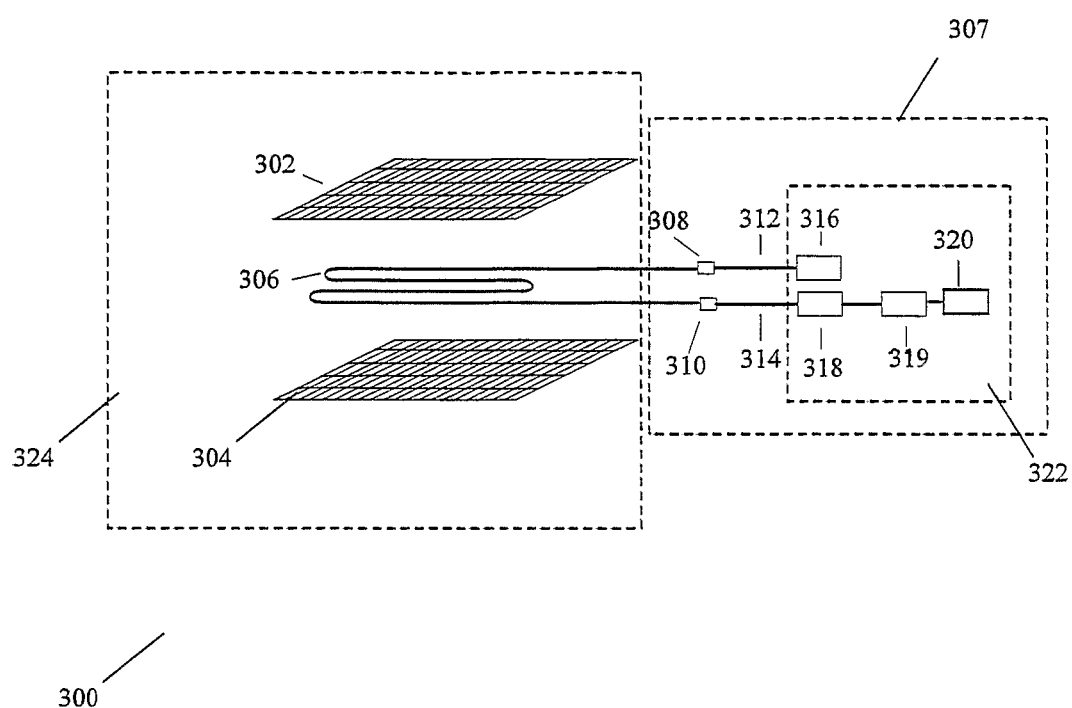
FIG. 3 is a schematic diagram illustrating a sensor system in an example embodiment.

FIG. 3 is a schematic diagram illustrating a sensor device/system 300 in an example embodiment. The system 300 comprises a top polyester fiber layer 302 and a bottom polyester fiber layer 304. The layers 302, 304 each comprise a mesh-like structure that can stretch over a large area. The system 300 further comprises a multimode optical fiber section 306 disposed between the layers 302, 304. The system 300 further comprises a detection unit 307. The detection unit in this embodiment comprises fiber connectors or splicing joints 308, 310 for connecting the section 306 to optical fibers 312, 314 respectively. The optical fibers 312, 314 can each be a multimode optical fiber or a single mode optical fiber. The optical fiber 312 is connected to a light source 316 and the optical fiber 314 is connected to a light detector 318 of the detection unit 307. The light detector 318 is connected to an amplifier 319 that is in turn connected to a signal processing unit 320 of the detection unit 307. The signal processing unit 320 comprises display and alarm functions for reporting vital signs parameters.

In the example embodiment, the mesh-like structures from layers 302, 304 form a mechanical structure for creating a microbending effect on the multimode optical fiber section 306. The mechanical structure can receive a pressure exerted by a person's body as a result of one or more of a group consisting of a movement of the person's body, a respiratory action of the person's body and a heart beat action of the person's body and can cause microbending of the multimode optical fiber under the exerted pressure. Thus, in the example embodiment, the multimode optical fiber is disposed between first and second sets of microbending elements of the mechanical structure substantially in a direction of the exerted pressure. In the example embodiment, the first set of microbending elements are comprised in the top layer 302 and the second set of microbending elements are comprised in the bottom layer 304.

In the example embodiment, the multimode optical fiber section 306 can comprise glass optical fiber, plastic optical fiber or other types of suitable optical fibers.

In the example embodiment, the light source 316, the light detector 318, the amplifier 319 and the signal processing unit 320 make up an interrogator unit 322. The polyester fiber layers 302,304 and the multimode optical fiber section 306 make up a sensor mat 324. Light from the light source 316 can be input through the fiber connector 308 into the section 306 of the sensor mat 324. The light source 316 can be a laser, a light emitting diode (LED) or any other broad band or narrow band light source. The light detector 318 is used to convert optical signals obtained from the optical fiber 314 to electronic signals. The electronic signals are then amplified in the amplifier 319. Data acquisition and analysis are performed by the signal processing unit 320.

In use, a periodic difference in pressure exerted by a subject on the sensor mat 324, due to e.g. breathing and/or heart beating, modulates light propagating along the multimode optical fiber section 306. For example, when a subject's back of body is placed on the sensor mat 324, the light is modulated according to the subject's movement. Information relating to breathing rate/heart beat/body movement can be obtained/detected by extracting and processing of the modulated light, extracted at the light detector 318 and transmitted into the signal processing unit 320.

In the example embodiment, the microbending effect is created by the mesh-like structure on each polyester fiber layer 302, 304. Fabrication of the sensor mat 324 is relative easy. The sensor mat 324 can be placed between a bed sheet and a mattress. It can also be embedded within a bed sheet or mattress. For seat applications, the sensor mat 324 can be placed in the back of a seat.

It will be appreciated that additional covers may be added respectively to polyester fiber layers 302, 304 for more robust protection.

Figure 4:
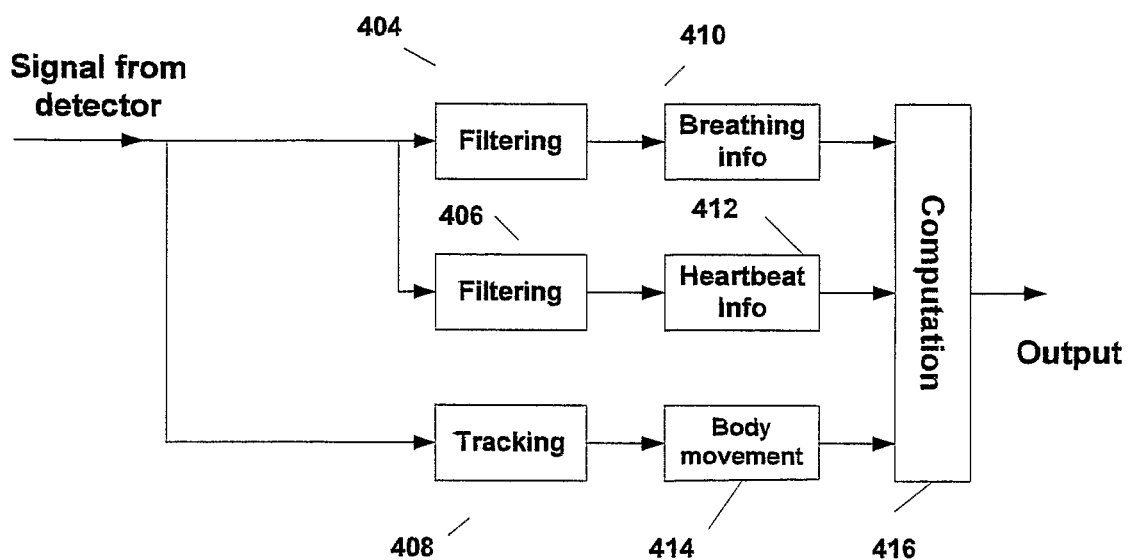
FIG. 4 is a schematic block diagram for illustrating processing of a modulated signal in a sensor device of an example embodiment.

FIG. 4 is a schematic block diagram for illustrating processing of a modulated signal in a sensor device of an example embodiment. An amplified extracted modulated signal from a light detector is obtained (compare light detector 318 and amplifier 319 of FIG. 3). The signal is transmitted into two types of filtering, shown schematically in blocks 404 and 406. The filtering 404 is used to eliminate noises attached to breathing signals while the filtering 406 to eliminate noises attached to heart beat signals. The filtering 404 may be achieved by processes such as but not limited to averaging, smoothing and low pass filtering. The filtering 406 may be achieved by processes such as but not limited to averaging, smoothing, subtracting, compressing and band pass filtering.

Before a body movement pattern is extracted from the signal obtained from the light detector, deviation tracking is carried out at block 408. The tracking at block 408 checks with respect to a reference signal obtained initially to determine if any body movement has been induced by a user on a sensor mat of the sensor device.

In the example embodiment, three different extractions, i.e. breathing information at block 410, heart beat information at block 412, and body movement information at block 414 are performed on the conditioned signals (i.e. resulting from blocks 404, 406 and 408 as shown) to obtain vital signs parameters. For example, the breathing information 410 can be obtained by peak/valley/amplitude detection or by Fast Fourier Transform or Wavelet analysis. The heart beat information 412 can be obtained by peak/valley/amplitude detection or by Fast Fourier Transform or Wavelet analysis. Subsequently, the extracted information may be further computed in block 416 to obtain intelligent information (e.g. changes in rates, comparison, alarms, etc.). The information can be transmitted thereafter for different applications. For applications associated with breathing information only, blocks 406, 412, 408, 414 can be excluded. For applications associated with heart beat information only, blocks 404, 410, 408, 414 can be excluded. For applications associated with body movement information only, blocks 406, 412, 404, 410 can be excluded.

For example, heart beat rate and breathing rate can be displayed in a display to keep observers informed on vital signs of a subject. In an event if breathing has ceased, a signal processing unit (compare signal processing unit 320 in FIG. 3) can trigger an alarm to alert other persons so that intervention can be introduced as soon as possible.

Further, computed information at block 416 can be sent via 3G or wireless fidelity (WIFI) networks in real time so that observers can keep track of the information while the subject can be at any part of the world where the sensor device is installed.

Figure 5:
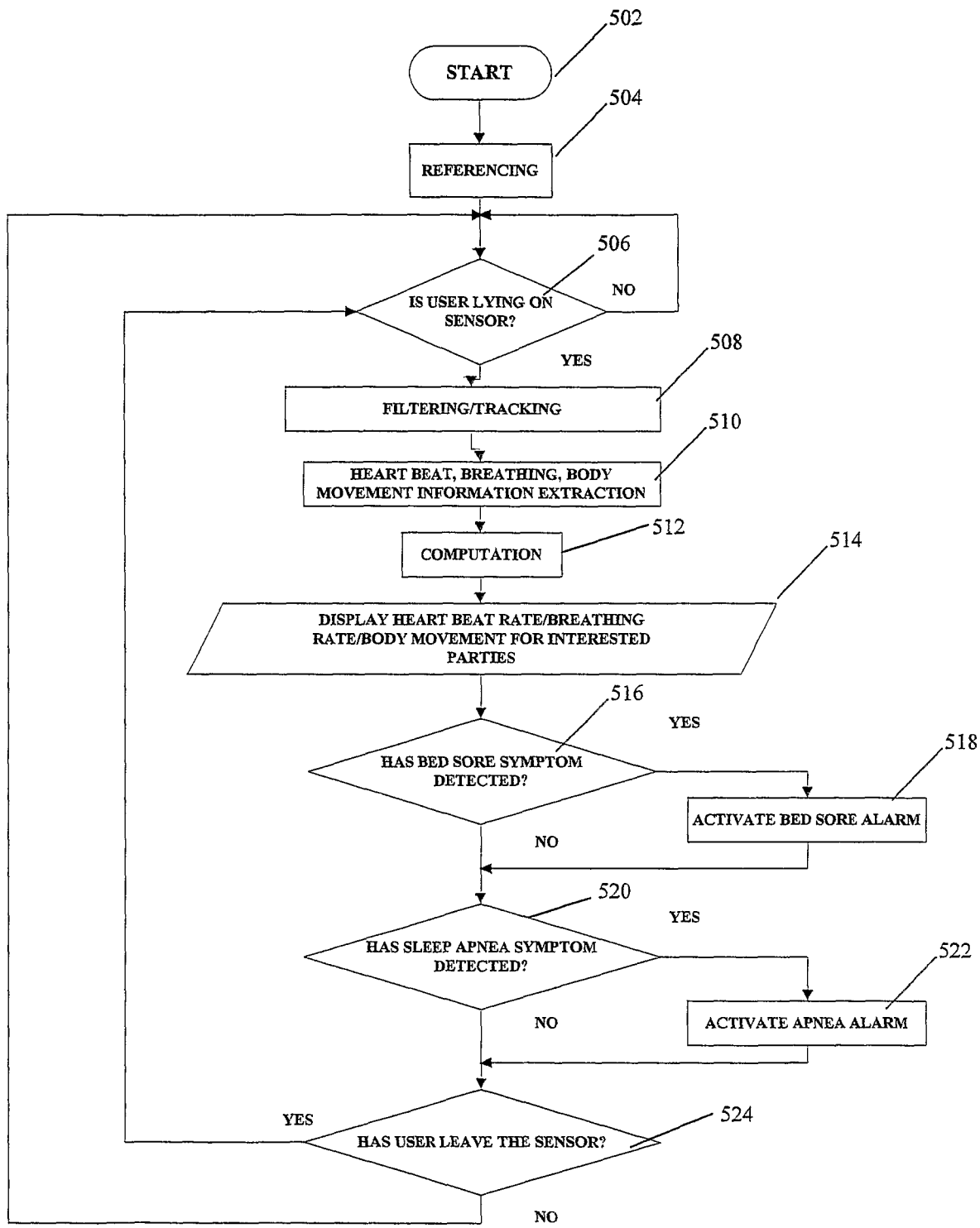
FIG. 5 is a schematic flow chart illustrating a work flow of a sensing device in an example embodiment.

FIG. 5 is a schematic flow chart illustrating a work flow of a sensing device in an example embodiment. The work flow may be implemented, for example, using a computer program executable by a computer processor in the sensing device.

At step 502, the work flow begins. At step 504, a referencing process is carried out so that idling characteristics of modulated light detected by a light detector of the sensing device is stored in a memory of the sensing device. The references or reference signals are used to determine if there is any user lying on a sensor of the sensing device or not. In addition, the reference signals are also be used to determine if the user has left the sensor or not.

At step 506, the signal detected from the light detector is used to check if the user is lying on the sensor. When there is no user lying on the sensor, computation is not carried out so most of activities of the sensing device is shut down. Once a user is confirmed to be lying on the sensor, a signal generated by the light detector is continuously used to compute heart beat rate, breathing rate and/or body movement.

At step 508, when a user is detected lying on the sensor in which detected light is modulated by the user, filtering applications and deviation tracking for body movement detection are carried out to obtain a pattern. Compare blocks 404, 406,408 of FIG. 4.

At step 510, the extraction of breathing/heart beat/body movement information is performed to obtain a useful signal. At step 512, computation is carried out on the signal from the light detector so that more useful applications such as activating an alarm can be triggered if desired. The applications can include storing useful data for further reference, sending information wirelessly via 3G/WIFI networks, displaying information that is useful for an observer in a display etc. Compare block 416 of FIG. 4.

It will be appreciated that after the user has been detected lying on the sensor, heart beat rate, breathing rate and/or body movement information is not immediately available for displaying on a display as there is typically not enough samples to produce reliable information. At step 514, after an interval, the computed breathing rate, heart beat rate and/or body movement information can be shown on a display panel for a user's viewing. For example but not by way of limitation, an interval can range from a few seconds to about 60 seconds. The body movement information can for example be movement patterns, number of body movements within a period of time, identification of alarming or erratic movements within a short period of time.

At step 516, information from step 514 is used to detect whether there is a bed sore symptom in the user. For example, if it is detected that the user is not showing any movement or only minor movements from one position in a time period of for example about 2 hours, there is a danger that the user may develop a bed sore. If a bed sore symptom is detected, at step 518, a bed sore alarm is triggered so that intervention can be carried out on the user. At step 520, information from step 514 is used to detect whether there is a sleep apnea symptom in the user. For example, if it is detected that the user has stopped breathing temporarily, there is a danger that the user may be having sleep apnea. If a sleep apnea symptom is detected, at step 522, an apnea alarm is triggered so that intervention can be carried out on the user. It will be appreciated that additional functions can also be implemented depending on requirements.

At step 524, information is continuously read from the light detector and computation is carried out continuously until the user has left the sensor.

After the user leaves the sensor, the work flow loops back to step 506 and the computation stops running. The computation starts running again when a user is detected to be lying on the sensor.

Figure 6:
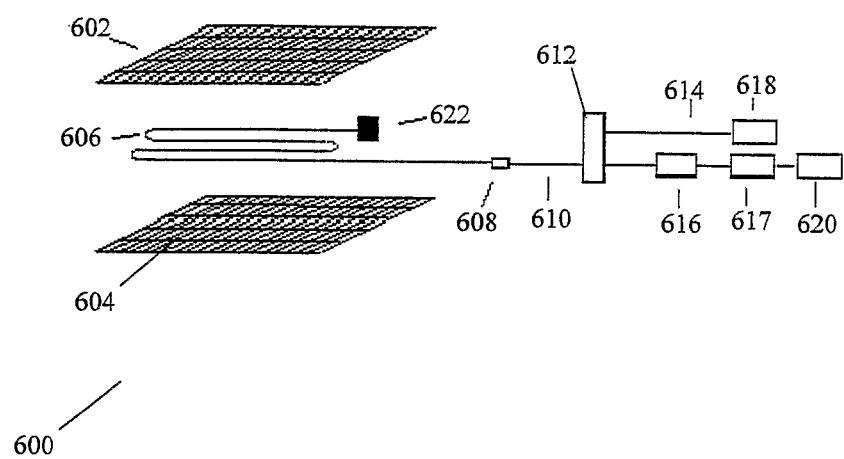
FIG. 6 is a schematic diagram illustrating a sensor system in an example embodiment.

FIG. 6 is a schematic diagram illustrating a sensor device/system 600 in an example embodiment. The system 600 comprises a top polyester fiber layer 602 and a bottom polyester fiber layer 604. The layers 602, 604 each comprise a mesh-like structure that can stretch over a large area. The system 600 further comprises a multimode optical fiber section 606 disposed between the layers 602, 604, and a fiber connector or splicing joint 608 for connecting the section 606 to an optical fiber 610. The system further comprises a 1×2 fiber coupler 612. The fiber coupler 612 connects the optical fiber 610 to an optical fiber 614 and also connects the optical fiber 610 to a detector 616. The detector 616 is connected to an amplifier 617. The optical fibers 610, 614 can each be a multimode optical fiber or a single mode optical fiber. The optical fiber 614 is connected to a light source 618. The detector 616 via the amplifier 617 is connected to a signal processing unit 620. The signal processing unit 620 comprises display and alarm functions for reporting vital signs parameters.

In the example embodiment, the system 600 further comprises a mirror 622 connected/attached to the section 606 for reflecting light traveling in the section 606 propagating from the light source 618 back to the detector 616.

In the example embodiment, the multimode optical fiber section 606 can comprise glass optical fiber, plastic optical fiber or other types of suitable optical fibers.

Figure 7:
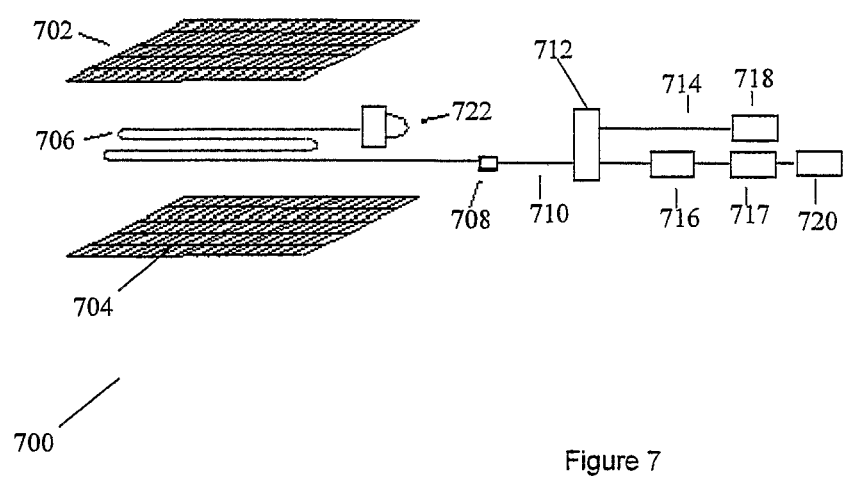
FIG. 7 is a schematic diagram illustrating a sensor system in an example embodiment.

FIG. 7 is a schematic diagram illustrating a sensor device/system 700 in an example embodiment. The system 700 comprises a top polyester fiber layer 702 and a bottom polyester fiber layer 704. The layers 702, 704 each comprise a mesh-like structure that can stretch over a large area. The system 700 further comprises a multimode optical fiber section 706 disposed between the layers 702, 704, and a fiber connector or splicing joint 708 for connecting the section 706 to an optical fiber 710. The system further comprises a 1×2 fiber coupler 712. The fiber coupler 712 connects the optical fiber 710 to an optical fiber 714 and also connects the optical fiber 710 to a detector 716. The detector 716 is connected to an amplifier 717. The optical fibers 710, 714 can each be a multimode optical fiber or a single mode optical fiber. The optical fiber 714 is connected to a light source 718. The detector 716 via the amplifier 717 is connected to a signal processing unit 720. The signal processing unit 720 comprises display and alarm functions for reporting vital signs parameters.

In the example embodiment, the system 700 further comprises a 1×2 coupler 722 (having its two output ends joined together) connected to the section 706 for reflecting light traveling in the section 706 propagating from the light source 718 back to the detector 716.

In the example embodiment, the multimode optical fiber section 706 can comprise glass optical fiber, plastic optical fiber or other types of suitable optical fibers.

Figure 8:
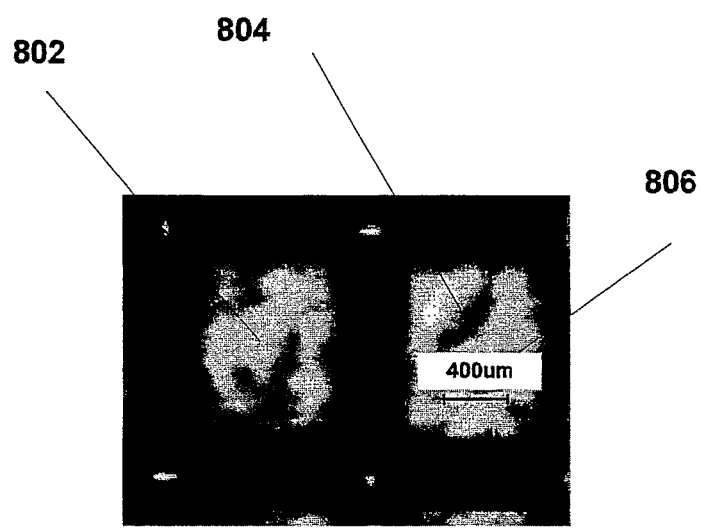
FIG. 8 is a top view picture illustrating an example of a mesh-like structure section of a sensor mat in an example embodiment.

FIG. 8 is a top view picture illustrating an example of a mesh-like structure section of a sensor mat in an example embodiment. The holes 802, 804 in the mesh can be square, rectangle or other shapes. The pitch of the mesh can range from a few hundred microns to a few millimeters although it can be smaller or larger. Preferably, if a large-area mesh structure is used, a multimode optical fiber with a longer length can be easily used to cover a subject body area while the sensitivity of the sensor mat can also be increased due to a longer interaction length with the subject.

Figure 9A:
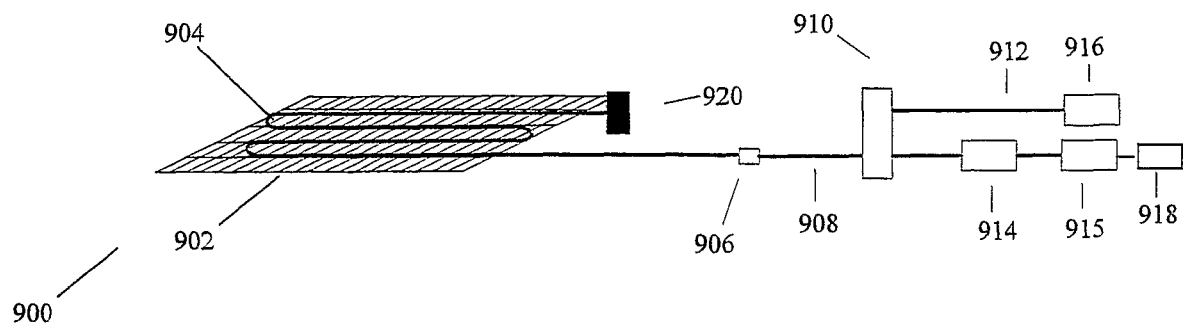
FIG. 9(a) is a schematic diagram illustrating a sensor system in an example embodiment.

FIG. 9(a) is a schematic diagram illustrating a sensor device/system 900 in an example embodiment. The system 900 comprises a polyester fiber layer 902 interwoven with a multimode optical fiber 904. The system 900 further comprises a fiber connector or splicing joint 906 for connecting the multimode optical fiber 904 to an optical fiber 908. The system further comprises a 1×2 fiber coupler 910. The fiber coupler 910 connects the optical fiber 908 to another optical fiber 912 and also connects the optical fiber 908 to a detector 914. The detector 914 is connected to an amplifier 915. The optical fibers 908, 912 can each be a multimode optical fiber or a single mode optical fiber. The optical fiber 912 is connected to a light source 916. The detector 914 via the amplifier 915 is connected to a signal processing unit 918. The signal processing unit 918 comprises display and alarm functions for reporting vital signs parameters.

In the example embodiment, the system 900 further comprises a mirror 920 connected to the multimode optical fiber 904 for reflecting light traveling in the multimode optical fiber 904 propagating from the light source 916 back to the detector 914.

In the example embodiment, the fiber layer 902 forms a mechanical structure for creating a microbending effect on the multimode optical fiber 904. The mechanical structure can receive a pressure exerted by a person's body as a result of one or more of a group consisting of a movement of the person's body, a respiratory action of the person's body and a heart beat action of the person's body and can cause microbending of the multimode optical fiber under the exerted pressure. Thus, in the example embodiment with the fiber layer 902 interwoven with the multimode optical fiber 904, the multimode optical fiber 904 is disposed between first and second sets of microbending elements of the mechanical structure substantially in a direction of the exerted pressure. In the example embodiment, the first set of microbending elements are disposed on a top surface of the multimode optical fiber (compare numeral 924 of FIG. 9(b)) and the second set of microbending elements are disposed on a bottom surface of the multimode optical fiber (compare numerals 926, 928 of FIG. 9(b)).

In the example embodiment, the multimode optical fiber 904 can comprise glass optical fiber, plastic optical fiber or other types of suitable optical fibers.

In use, the polyester fiber layer 902 interwoven with the multimode optical fiber 904 functions as a fiber mode converter.

Figure 9B:
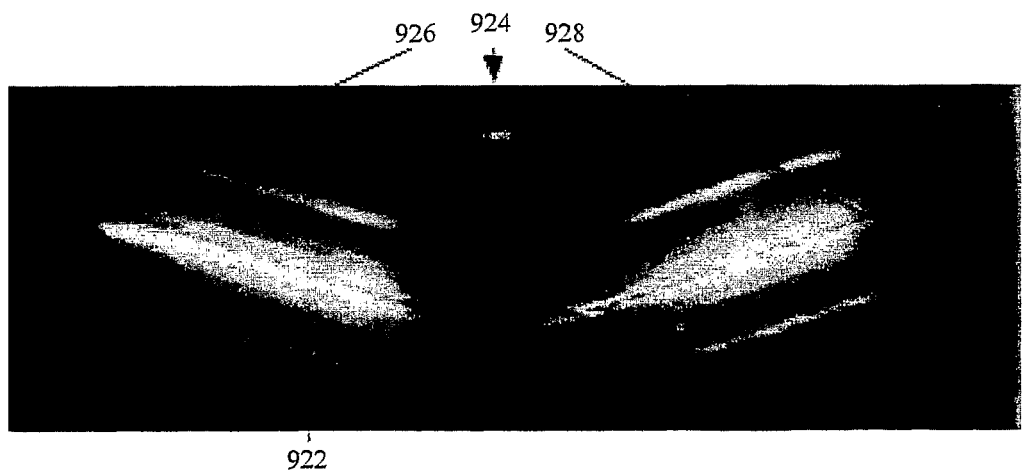
FIG. 9(b) is a picture illustrating polyester fiber layer interwoven with a multimode optical fiber in an example embodiment.

FIG. 9(b) is a picture illustrating a polyester fiber layer interwoven with a multimode optical fiber in an example embodiment. The polyester fiber layer interwoven with the multimode optical fiber forms a fiber mode converter (FMC). In the example embodiment, a section of a multimode optical fiber 922 and polyester fibers parts 924, 926, 928 are weaved together to form the FMC. The pitch of the FMC can be, for example but not by way of limitation, about 1 mm to a few millimeters. The multimode optical fiber 922 can comprise glass fiber, plastic fiber or other optical fibers. A top and bottom layer cover can be used to protect the FMC structure of FIG. 9(b), to form a sensor mat by using conventional molding and sealing methods.

The FMC is a device for stabilizing modes propagating in the multimode optical fiber 922 by bending the optical fiber 922 that causes efficient mode coupling. There are a plurality of modes propagated in the multimode optical fiber 922 and any external perturbations on the optical fiber 922 can cause a redistribution of modal power. When the multimode optical fiber 922 is bent, light transmitted along the optical fiber 922 may attenuate. Bending losses in multimode fibers can be used to obtain desired information.

For example, when the multimode optical fiber 922 is imposed with curvature bends, the light loss increases with the number of bending lengths and as the bending radius decreases.

Furthermore, by disposing the multimode optical fiber between first and second sets of microbending elements of the mechanical structure, the microbending effect achievable can be increased. This can provide advantages over a configuration providing bending elements acting on only one side of a fiber such as a configuration with an optical fiber disposed on a layer of microbending elements.

Figure 10:
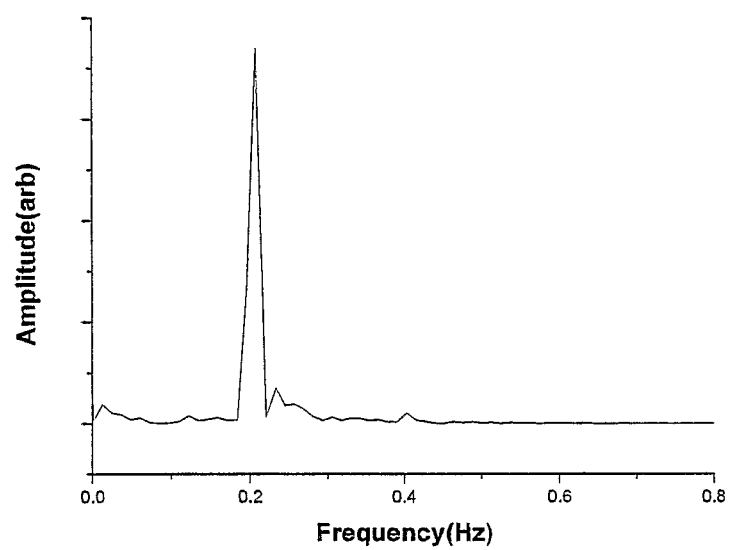
FIG. 10 is an example frequency spectrum graph showing a measured breathing signal in an example embodiment.

FIG. 10 is an example frequency spectrum graph showing a measured breathing signal in an example embodiment. The breathing signal is measured from a user when the user is sitting down on a chair and when a sensor mat is placed on the user's back. The graph shows that the user is breathing at a frequency of about 0.2 Hz. In other words, the breathing rate is about 12 times per minute.

Figure 11:
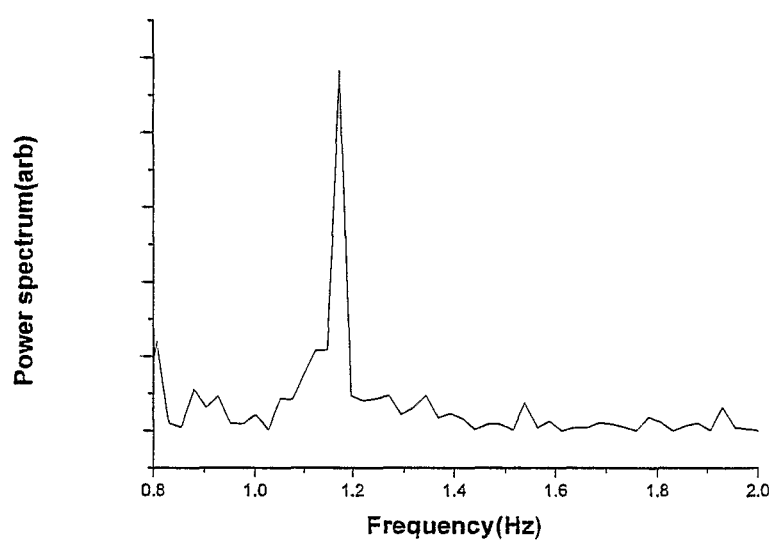
FIG. 11 is an example frequency spectrum graph showing a measured heart beat signal in an example embodiment.

FIG. 11 is an example frequency spectrum graph showing a measured heart beat signal in an example embodiment. The heart beat signal is measured from a user when a sensor mat is placed on the user's back. The graph shows that the heart beat signal is at a frequency of between about 1.1 to 1.2 Hz (about 1.17 Hz). In other words, the heart beat rate is about 70 beats per minute.

Figure 12:
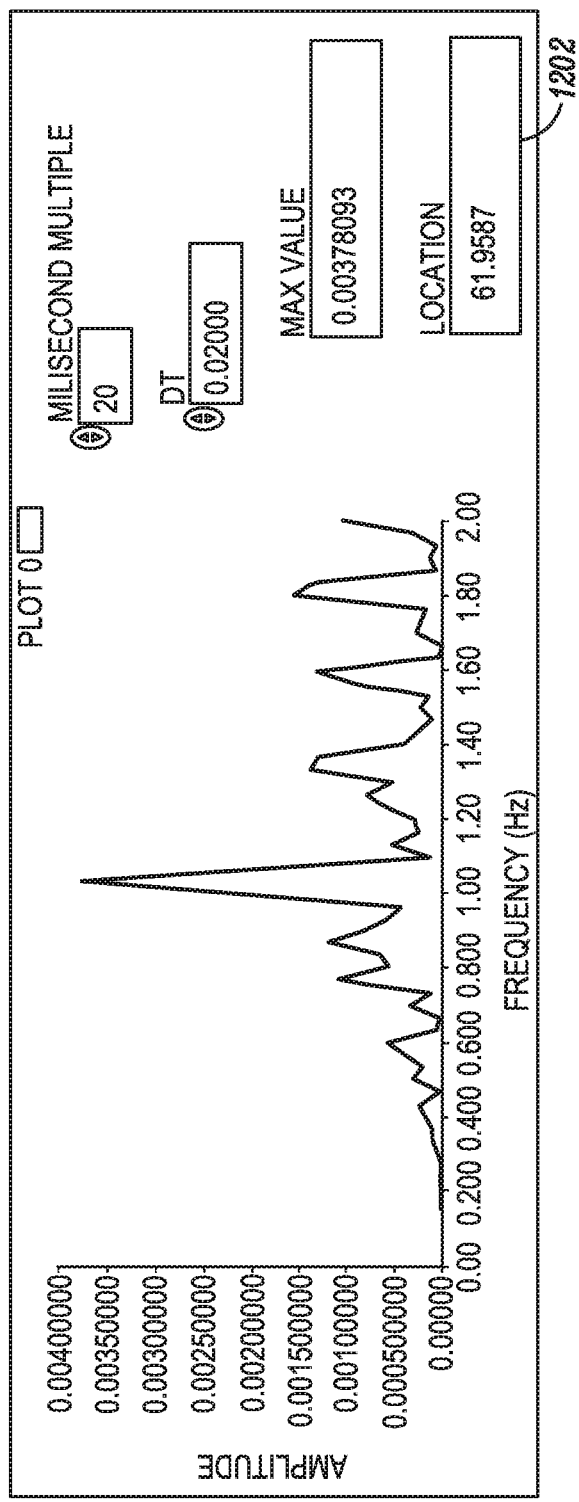
FIG. 12 is a frequency spectrum measurement of a heart beat signal of a first person in an example embodiment.
Figure 13:
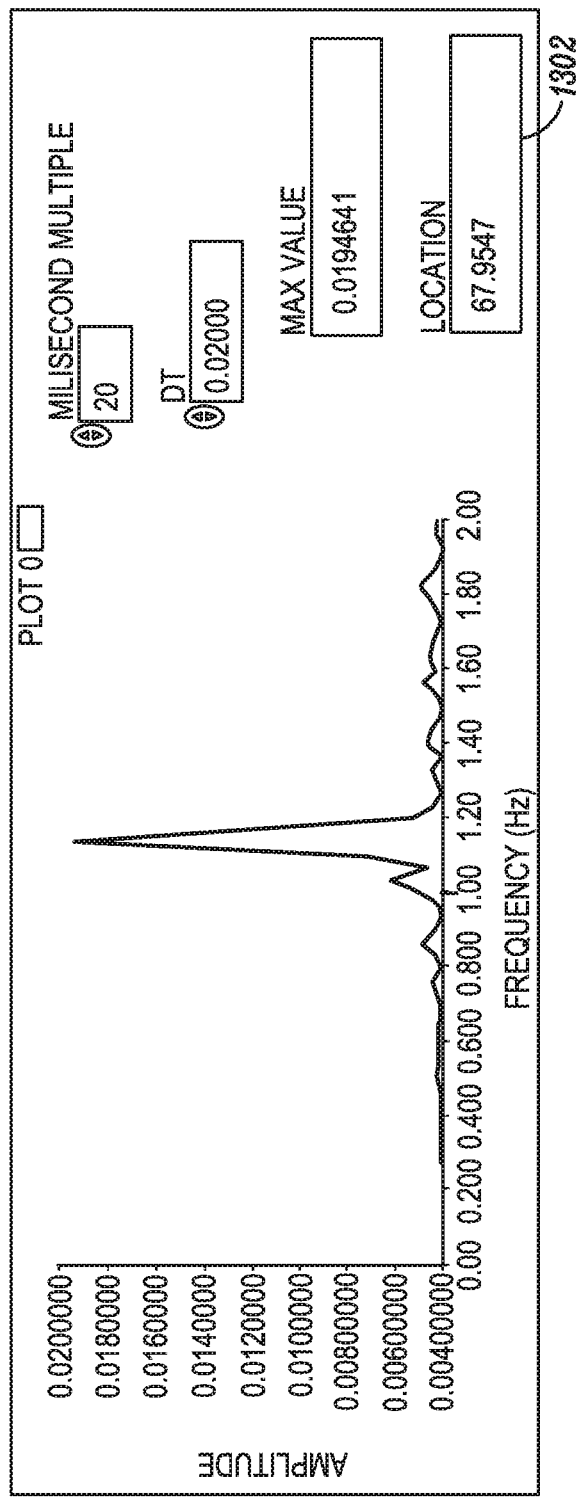
FIG. 13 is a frequency spectrum measurement of a heart beat signal of a second person in an example embodiment.

FIG. 12 is a frequency spectrum measurement of a heart beat signal of a first person in an example embodiment. FIG. 13 is a frequency spectrum measurement of a heart beat signal of a second person in an example embodiment. The signals were measured from the first and second persons while the persons were sitting down on chairs and with sensor mats placed on the back rests against the persons' backs. It can be seen that the both persons' heart beat signals were measured correctly. From FIG. 12, the frequency with peak amplitude measured is about 1.03 Hz. This was about 61.9587 heart beats per minute (heart beat rate shown on the FIG. 12 at numeral 1202). From FIG. 13, the frequency with peak amplitude measured is about 1.13 Hz. This was about 67.9547 heart beats per minute (heart beat rate shown on the FIG. 13 at numeral 1302).

Figure 14:
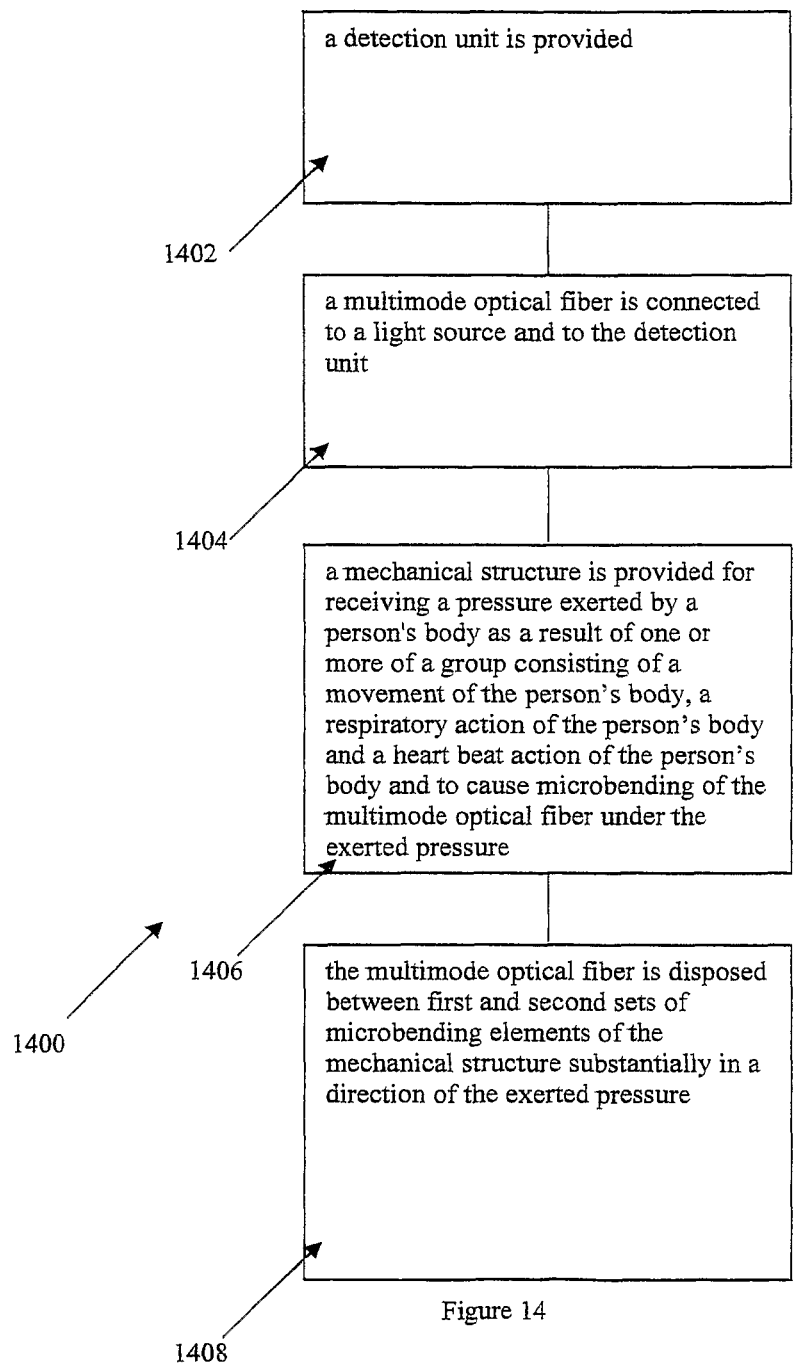
FIG. 14 is a schematic flowchart illustrating a method for detecting vital signs in an example embodiment.

FIG. 14 is a schematic flowchart 1400 illustrating a method for detecting vital signs in an example embodiment. At step 1402, a detection unit is provided. At step 1404, a multimode optical fiber is connected to a light source and to the detection unit. At step 1406, a mechanical structure is provided for receiving a pressure exerted by a person's body as a result of one or more of a group consisting of a movement of the person's body, a respiratory action of the person's body and a heart beat action of the person's body and to cause microbending of the multimode optical fiber under the exerted pressure. At step 1408, the multimode optical fiber is disposed between first and second sets of microbending elements of the mechanical structure substantially in a direction of the exerted pressure.

Figure 17:
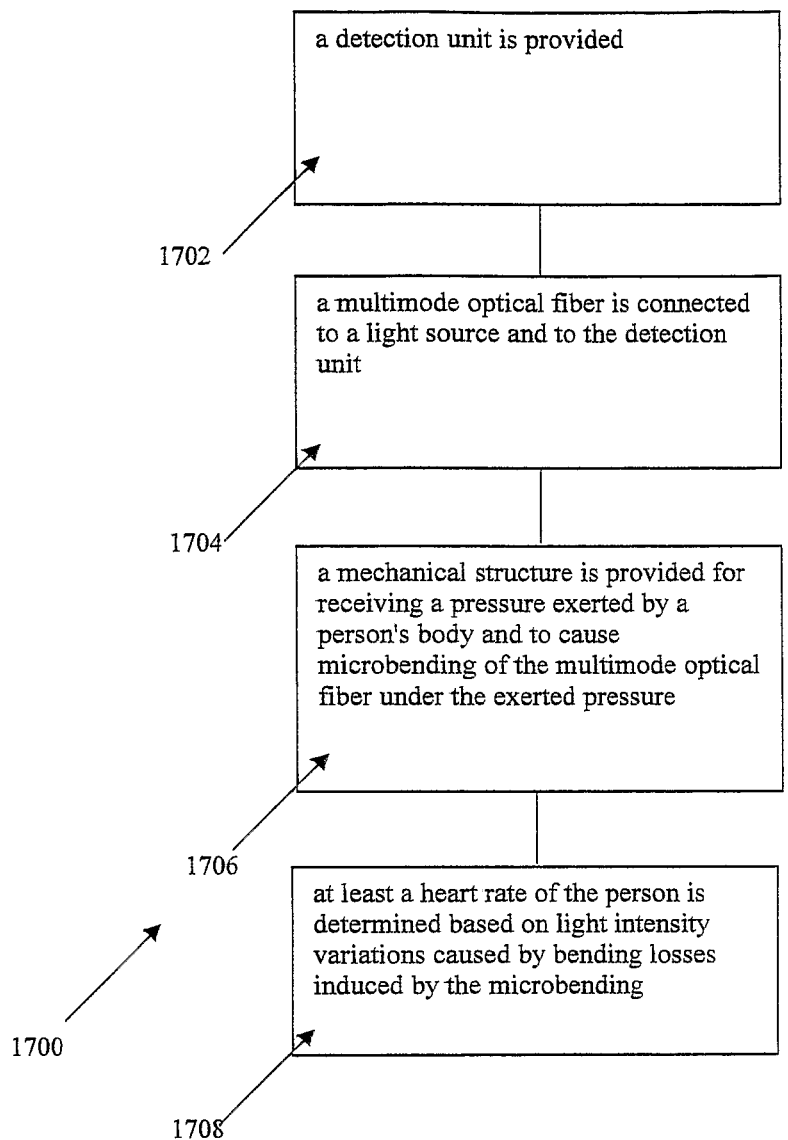
FIG. 17 is a schematic flowchart illustrating a method for detecting vital signs in an example embodiment.

FIG. 17 is a schematic flowchart 1700 illustrating a method for detecting vital signs in an example embodiment. At step 1702, a detection unit is provided. At step 1704, a multimode optical fiber is connected to a light source and to the detection unit. At step 1706, a mechanical structure is provided for receiving a pressure exerted by a person's body and to cause microbending of the multimode optical fiber under the exerted pressure. At step 1708, at least a heart rate of the person is determined based on light intensity variations caused by bending losses induced by the microbending.

Figure 15:
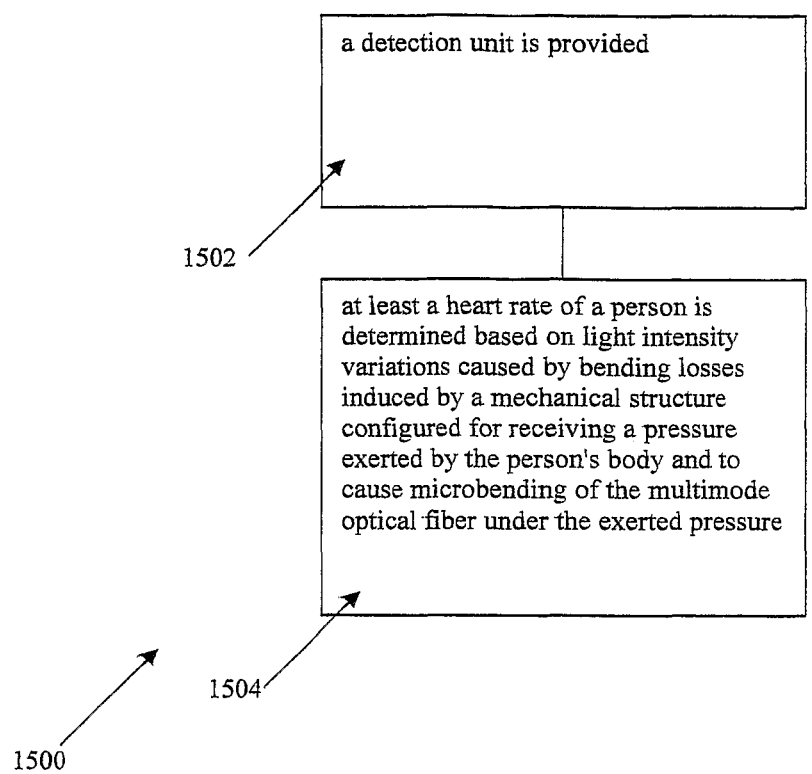
FIG. 15 is a schematic flowchart illustrating a method for vital signs detection in an example embodiment.

FIG. 15 is a schematic flowchart 1500 illustrating a method for vital sighs detection in an example embodiment. The method can be executed by a computing device. In the example embodiment, a data storage medium having computer code means stored thereon is used to instruct the computing device to execute the method. In FIG. 15, at step 1502, an optical signal is received from a multimode optical fiber. At step 1504, at least a heart rate of a person is determined based on light intensity variations caused by bending losses induced by a mechanical structure configured for receiving a pressure exerted by the person's body and to cause microbending of the multimode optical fiber under the exerted pressure.

Figure 16:
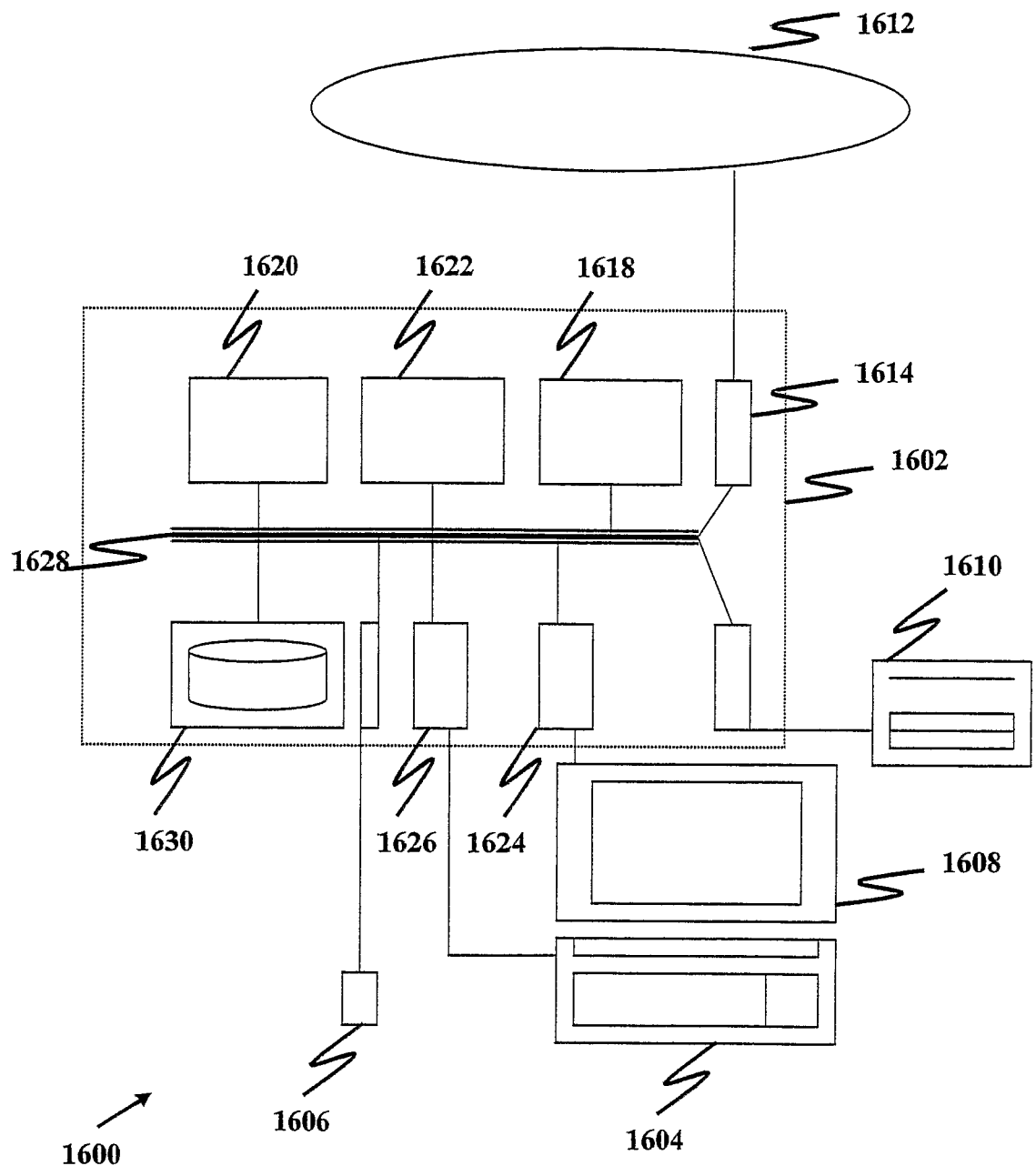
FIG. 16 is a schematic diagram of a computer system for implementing a method and system of an example embodiment.

The method and system of the example embodiments can be implemented using a computer system 1600, schematically shown in FIG. 16. For example, the signal processing unit of example embodiments may take the form of the described computer system. The method and system may be implemented as software, such as a computer program being executed within the computer system 1600, and instructing the computer system 1600 to conduct the method of the example embodiments.

The computer system 1600 comprises a computer module 1602, input modules such as a keyboard 1604 and mouse 1606 and a plurality of output devices such as a display 1608, and an alarm 1610.

The computer module 1602 is connected to a computer network 1612 via a suitable transceiver device 1614, to enable access to e.g. the Internet or other network systems such as Local Area Network (LAN) or Wide Area Network (WAN).

The computer module 1602 in the example includes a processor 1618, a Random Access Memory (RAM) 1620 and a Read Only Memory (ROM) 1622. The computer module 1602 also includes a number of Input/Output (I/O) interfaces, for example I/O interface 1624 to the display 1608, and I/O interface 1626 to the keyboard 1604.

The components of the computer module 1602 typically communicate via an interconnected bus 1628 and in a manner known to the person skilled in the relevant art.

The application program is typically supplied to the user of the computer system 1600 encoded on a data storage medium such as a CD-ROM or flash memory carrier and read utilising a corresponding data storage medium drive of a data storage device 1630. The application program is read and controlled in its execution by the processor 1618. Intermediate storage of program data maybe accomplished using RAM 1620.

The above described example embodiments can provide a device and method whereby no electricity is used in a sensor seat or bed. The measurements provided by the described example embodiments are non-intrusive. Also, described example embodiments can provide a cost-effective solution which is similar on scale to electric sensors. The above described example embodiments can provide a relatively simpler signal interrogation as compared to other fiber optical systems. Also, the above described example embodiments can provide a relatively simpler system configuration as compared to other sensing systems. In addition, the above described example embodiments can provide relatively simpler and better comfortability to users than systems using stick-on sensors etc.

The above described example embodiments can provide a sensing device for detecting vital signs parameters of a bedded/seated person. It can be easy to integrate such a sensing device to a smart bed/smart chair which can give rise to potential applications in healthcare (e.g. sleep monitoring, vital signs monitoring etc.), home automation (e.g. home appliances control for smart homes etc.) and, non-drug solutions to e.g. lower high blood pressure. Also, the above described example embodiments can provide an intrinsically safe sensing, device and method.

In the example embodiments, the sensor mat is described having two layers of polyester fibers. However, it will be appreciated that the sensor mat is not limited as such and can include any sensor member that can create a microbending effect on a multimode optical fiber.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A vital signs detecting device, the device comprising,
   a multimode optical fiber;
   a light source for inputting light into the multimode optical fiber;
   a light detection unit for detecting light modulation in the multimode optical fiber;
   a first 1×2 fiber coupler for connecting the light source and the light detection unit to the multimode optical fiber at a first end of the multimode optical fiber; and
   a mechanical structure configured for disposition between a person's body and a support surface so as to receive a pressure exerted by the person's body as a result of one or more of a group consisting of a movement of the person's body, a respiratory action of the person's body and a heart beat action of the person's body, the mechanical structure including first and second sets of microbending elements to cause microbending of the multimode optical fiber and associated bending losses under the exerted pressure, wherein the first set of microbending elements are comprised in a first layer of the mechanical structure and the second set of microbending elements are comprised in a second layer of the mechanical structure;
   wherein the multimode optical fiber is disposed between the first set of microbending elements in the first layer of the mechanical structure and the second set of microbending elements in the second layer of the mechanical structure substantially in a direction of the exerted pressure; and
   wherein the light detection unit is adapted for determining the one or more of the movement of the person's body, the respiratory action of the person's body and the heart beat action of the person's body based on light intensity variations caused by bending losses induced by the microbending.

2. The device as claimed in claim 1, wherein the first and second layers each comprise a mesh-like structure.

3. The device as claimed in claim 1, wherein the mechanical structure is interwoven with the multimode optical fiber such that the first set of microbending elements are disposed on a top surface of the multimode optical fiber and the second set of microbending elements are disposed on a bottom surface of the multimode optical fiber.

4. The device as claimed in claim 3, wherein the mechanical structure comprises a mesh-like structure.

5. The device as claimed in claim 1, further comprising a mirror attached to the multimode optical fiber at a second end thereof for reflecting light to the first end of the multimode optical fiber.

6. The device as claimed in claim 1, further comprising a second 1×2 fiber coupler connected to the multimode optical fiber at a second end thereof, the second 1×2 fiber coupler configured for redirecting light to the first end of the multimode optical fiber.

7. A method for detecting vital signs, the method comprising,
    inputting light into a first end of a multimode optical fiber;
    providing a mechanical structure for disposition between a person's body and a support surface so as to receive a pressure exerted by the person's body as a result of one or more of a group consisting of a movement of the person's body, a respiratory action of the person's body and a heart beat action of the person's body and for causing microbending of the multimode optical fiber and associated bending losses under the exerted pressure, wherein the mechanical structure comprises a first layer and a second layer, and wherein the multimode optical fiber is disposed between the first and second layers and, more particularly, between a first set of microbending elements comprised in the first layer of the mechanical structure and a second set of microbending elements comprised in the second layer of the mechanical structure, substantially in a direction of the exerted pressure; and
    detecting light modulation in the multimode optical fiber by a detector coupled to the multimode optical fiber and receiving the light therefrom to determine the one or more of the movement of the person's body, the respiratory action of the person's body and the heart beat action of the person's body based on light intensity variations caused by bending losses induced by the microbending.

8. The method as claimed in claim 7, wherein the step of detecting light modulation in the multimode optical fiber comprises the detector detecting light modulation extracted from the first end of the multimode optical fiber, the method further comprising reflecting light from a second end of the multimode optical fiber to the first end of the multimode optical fiber.

* * * * *